(12) United States Patent
Laufer

(10) Patent No.: US 8,118,767 B2
(45) Date of Patent: Feb. 21, 2012

(54) GASTROINTESTINAL IMPLANT AND METHODS FOR USE

(76) Inventor: Michael D. Laufer, Menlo Park, CA (US)

( * ) Notice: Subject to any disclaimer, the term of this patent is extended or adjusted under 35 U.S.C. 154(b) by 584 days.

(21) Appl. No.: 12/203,030

(22) Filed: Sep. 2, 2008

(65) Prior Publication Data

US 2009/0062717 A1    Mar. 5, 2009

Related U.S. Application Data

(63) Continuation of application No. PCT/US2007/063140, filed on Mar. 2, 2007.

(60) Provisional application No. 60/779,062, filed on Mar. 2, 2006.

(51) Int. Cl.
*A61M 5/00* (2006.01)
*A61F 2/04* (2006.01)

(52) U.S. Cl. .............................. 604/8; 604/9; 623/23.68

(58) Field of Classification Search .................. 604/8, 9, 604/264; 623/23.68
See application file for complete search history.

(56) References Cited

U.S. PATENT DOCUMENTS

| | | |
|---|---|---|
| 3,818,511 A | 6/1974 | Goldberg et al. |
| 4,134,405 A | 1/1979 | Smit |
| 4,315,509 A | 2/1982 | Smit |
| 4,501,264 A | 2/1985 | Rockey |
| 4,548,201 A | 10/1985 | Yoon |
| 4,641,653 A | 2/1987 | Rockey |
| 4,648,383 A | 3/1987 | Angelchik |
| 4,719,916 A | 1/1988 | Ravo |
| 4,878,905 A | 11/1989 | Blass |
| 5,306,300 A | 4/1994 | Berry |
| 5,356,416 A | 10/1994 | Chu et al. |
| 5,425,765 A | 6/1995 | Tiefenbrun et al. |
| 5,489,295 A | 2/1996 | Piplani et al. |
| 5,540,713 A | 7/1996 | Schnepp-Pesch et al. |
| 5,676,696 A | 10/1997 | Marcade |
| 5,820,584 A | 10/1998 | Crabb |
| 5,876,450 A | 3/1999 | Johlin |
| 5,904,697 A | 5/1999 | Gifford, III et al. |
| 6,117,167 A | 9/2000 | Goicoechea et al. |
| 6,132,471 A | 10/2000 | Johlin, Jr. |
| 6,543,456 B1 | 4/2003 | Freeman |
| 6,546,280 B2 | 4/2003 | Osborne |
| 6,572,629 B2 | 6/2003 | Kalloo et al. |
| 6,582,472 B2 | 6/2003 | Hart |
| 6,675,809 B2 | 1/2004 | Stack et al. |

(Continued)

FOREIGN PATENT DOCUMENTS

WO  WO 2005/037073   4/2005

OTHER PUBLICATIONS

U.S. Appl. No. 10/687,954, filed Oct. 17, 2003 in the name of Laufer, Non-final Office Action mailed Apr. 10, 2006.

(Continued)

*Primary Examiner* — Leslie Deak
(74) *Attorney, Agent, or Firm* — Levine Bagade Han LLP

(57) ABSTRACT

Methods and devices for modifying the location at which bodily fluids interact with nutrients in a gastrointestinal tract having a conduit having a first end and a second end, the first end configured to divert bodily fluids from an entrance within a gastrointestinal tract to a location downstream from the entrance, and means for attaching the second end to the entrance.

39 Claims, 10 Drawing Sheets

U.S. PATENT DOCUMENTS

| | | | |
|---|---|---|---|
| 6,740,121 | B2 | 5/2004 | Geitz |
| 6,918,871 | B2 | 7/2005 | Schulze |
| 6,946,002 | B2 | 9/2005 | Geitz |
| 7,025,791 | B2 | 4/2006 | Levine et al. |
| 7,037,344 | B2 | 5/2006 | Kagan et al. |
| 7,220,284 | B2 | 5/2007 | Kagan et al. |
| 7,267,694 | B2 | 9/2007 | Levine et al. |
| 7,316,716 | B2 | 1/2008 | Egan |
| 7,354,454 | B2 | 4/2008 | Stack et al. |
| 7,476,256 | B2 | 1/2009 | Meade et al. |
| 2003/0032967 | A1 | 2/2003 | Park et al. |
| 2003/0040804 | A1 | 2/2003 | Stack et al. |
| 2003/0065359 | A1 | 4/2003 | Weller et al. |
| 2003/0109931 | A1 | 6/2003 | Geitz |
| 2003/0199989 | A1 | 10/2003 | Stack et al. |
| 2004/0039452 | A1 | 2/2004 | Bessler |
| 2004/0092892 | A1 | 5/2004 | Kagan et al. |
| 2004/0092974 | A1* | 5/2004 | Gannoe et al. ............... 606/153 |
| 2004/0107004 | A1 | 6/2004 | Levine et al. |
| 2004/0117031 | A1 | 6/2004 | Stack et al. |
| 2004/0122456 | A1 | 6/2004 | Saadat et al. |
| 2004/0133147 | A1 | 7/2004 | Woo |
| 2004/0249362 | A1 | 12/2004 | Levine et al. |
| 2005/0022827 | A1 | 2/2005 | Woo et al. |
| 2005/0038415 | A1 | 2/2005 | Rohr et al. |
| 2005/0043817 | A1* | 2/2005 | McKenna et al. .......... 623/23.65 |
| 2005/0085787 | A1 | 4/2005 | Laufer |
| 2005/0187566 | A1 | 8/2005 | Byrum |
| 2005/0228504 | A1 | 10/2005 | Demarais |
| 2005/0256587 | A1 | 11/2005 | Egan |
| 2006/0020247 | A1 | 1/2006 | Kagan et al. |
| 2006/0106332 | A1 | 5/2006 | Knudson et al. |
| 2006/0142787 | A1 | 6/2006 | Weller et al. |
| 2006/0206063 | A1 | 9/2006 | Kagan et al. |
| 2007/0282453 | A1* | 12/2007 | Weitzner et al. ............. 623/23.7 |
| 2008/0269662 | A1 | 10/2008 | Vassiliades et al. |
| 2009/0062717 | A1 | 3/2009 | Laufer |

OTHER PUBLICATIONS

U.S. Appl. No. 11/546,458, filed Oct. 10, 2006 in the name of Laufer, Response to non-final Office Action dated Feb. 18, 2010.
http://en.wikipedia.org/wiki/Nitinol (online encyclopedia, accessed Sep. 21, 2011).

* cited by examiner

US 8,118,767 B2

GASTROINTESTINAL IMPLANT AND METHODS FOR USE

CROSS-REFERENCE TO RELATED APPLICATIONS

This application is a continuation of PCT International Application No. PCT/US2007/063140 filed Mar. 2, 2007 which claims the benefit under 35 U.S.C. §119(e) of U.S. Provisional Application No. 60/779,062 filed Mar. 2, 2006, the contents of both applications are incorporated herein by reference.

BACKGROUND OF THE INVENTION

The incidence of obesity in the United States is significantly increasing causing an associated increase in obesity-related health problems. Because of this trend, efforts to control obesity are gaining the increased attention of both the medical community and the general public. However, while there may be a considerable number of individuals that are markedly overweight, a fraction of these individuals are currently eligible for surgery to reconstruct their gastrointestinal (GI) tract in order to control their weight. These GI procedures are reserved for the severely obese because of the significant complications associated with the surgery. Because these procedures often involve invasive surgery, the recuperation time is significant not to mention the possibility of complications which include the risk of death. It is estimated that without GI reconstruction, eligible patients face an annual mortality as high as 30%-50%. Obviously such a high risk of death justifies the use of these surgical procedures. It is contemplated that less invasive procedures would be better suited for the severely obese as well as those moderately or less obese.

FIG. 1A is an illustration of the digestive system. The digestive tract is a disassembly line in which food breaks down to become less and less complex so that nutrients become available to the body. As the food passes through the digestive tract, it mixes with other fluids to create a fluid mix. Below the esophagus 16, the (GI) tract expands to form the stomach 18. In the stomach 18 mechanical and chemical breakdowns of proteins occurs such that food leaves the stomach converted into a substance called chyme. From the stomach 18, the chyme, enters the small intestine 20 where secretions from the liver 22 and the pancreas 24 complete the digestive process.

The liver 22 produces which is then stored in the gall bladder 26. Bile is a complex mixture of essentially emulsifiers and surfactants that the body uses to absorb fat. Without bile, dietary fat is relatively insoluble and would pass out of the body as feces. The pancreas produces pancreatic enzymes which the body uses to digest and absorb proteins, and to a lesser degree, carbohydrates. Pancreatic enzymes move from the pancreas to the intestine through the pancreatic duct 28 which, in most individuals, combines with the bile duct 32 from the gall bladder 26 to form a common duct that enters the intestine through the Ampula of Vater 30 (also called the Ampulla of Vater, hepatopancreatic ampulla, ampulla biliaropancreatica). However, in some individuals, the bile duct 32 and pancreatic duct 28 remain separate and enter the small intestine 20 at separate location.

As the food fluid journeys through the small intestine 20, digested foodstuff, such as fats, are absorbed through the mucosal cells into both the capillary blood and the lacteal 38. Other digested foodstuffs, such as amino acids, simple sugars, water, and ions are absorbed by the hepatic portal vein 40.

From the small intestine 20, the remainder of the food fluid enters the large intestine 42 whose major function is to dry out indigestible food residues and eliminate them from the body as feces 44 through the anal canal 46.

Current gastrointestinal tract surgeries require incisions to be made into the abdomen in order to attach the distal small intestine to the stomach and to make the stomach smaller. This procedure is sometimes called "Roux-en-Y" or gastrojejunal bypass with gastric reduction. The procedure is commonly performed through a large midline abdominal incision, although some surgeons have developed adequate skill to perform the procedure through a number of smaller incisions in a laparoscopic manner with cameras and instruments inserted through the holes for visualization. Both methods cause weight loss through bypass by reducing the effective length of intestine available for the absorption of food and the stomach is reduced in size so that the patient cannot eat a lot of food. However, both methods require anesthesia (usually general), a prolonged recovery time, and are not reversible once the target weight of the patient is reached.

Another procedure used is vertical stapled gastroplasty. This procedure involves incision of the anterior abdominal wall and creation of a 10-15 ml pouch from the proximal stomach by use of 3-4 staples. This procedure also has numerous complications including rupture of the staple line, infection of the surgical incision, post operative hernias and the like. Moreover, due to the large amount of fat tissue in the anterior abdominal wall in the typical patient on whom this procedure is performed, poor healing of the operative wound may result. Furthermore prolonged post-operative bed rest after such extensive surgery predisposes obese patients to the development of deep vein thrombosis and possible pulmonary emboli, some with a potentially lethal outcome.

U.S. Pat. No. 6,740,121 describes an intragastric stent, U.S. Published applications 2004/0249362A1 and 2004/0107004A1 discloses sleeves for use in the small intestines. However, these devices do not provide a reservoir in the sleeve/stent. As a bolus of food passes through the small intestines, the bolus may block the ducts supplying the digestive fluids and/or conduit. These fluids may then be forced around the sleeve and/or stent. Such a condition may also cause the sleeve/stent to become dislodged within the small intestines.

Thus, there is a need for a device, method, and system to reduce weight that is less traumatic, has less recovery time, is reversible, not complicated, and is simple to perform. Additionally, there is a need for a device and method, and system that provides a reservoir for digestive fluids.

BRIEF SUMMARY OF THE INVENTION

Devices and methods are described for modifying the location at which bodily fluids interact with nutrients in a gastrointestinal tract using an implant having a conduit and fasteners to divert bodily fluids from an entrance within a gastrointestinal tract to a location downstream from the entrance.

The invention includes methods and devices for diverting fluid from a single or multiple ducts in a wall of a small intestine by inserting a support frame into the small intestines, the support frame having an opening in a wall and having an elongate conduit member coupled the support frame. The elongate conduit generally includes a near portion and a far portion and a lumen extending there between, where the lumen is in fluid communication with the side opening of the support frame at a location between the near and far portions causing the near portion and far portion of the conduit span across the side opening in the support frame such that the near portion remains proximal to the side opening, the elongate conduit further having at least one distal opening in the far portion. The side opening of the device is aligned with the duct such that fluid from the duct enters the elongate conduit lumen.

Devices for use with the invention include a support frame having a wall defining a passageway, where the wall includes at least one opening, an elongate conduit having a near portion and a far portion and body extending there between, a lumen extending there between, where the lumen is in fluid communication with the side opening of the support frame at a location between the near and far portions causing the near portion and far portion of the conduit to span across the side opening in the support frame such that the near portion remains proximal to the side opening, and at least one distal opening in the far portion of the elongate member.

Additional variations of the invention include one or more kits for bypassing intestinal fluids from the digestive tract comprising a scope-type device and an intestinal implant in accordance with those variations described herein.

The invention also an intestinal implant for preventing the interaction of fluid with a portion of the small intestines comprising a body means for diverting fluid from the opening in the intestines, a passage means or conduit for conveying fluid to a distal location in the intestines, a securing means for securing the implant to a wall of the intestines. The securing means may comprise the fasteners discussed herein or may comprise other methods of securing the implant to the intestinal wall as also discussed herein.

Although not required, the devices described herein may be implanted in a minimally invasive manner using a scope directed through a natural body opening (such as a gastro-intestinal opening). It should be noted that any discussions of a scope or endoscope are intended to include the endoscope, colonoscope, duodenoscope, and any other scope type device that is functionally able to implant the device.

It is noted that the subject application generally discusses transporting digestive fluids from a single duct within the small intestines. It is within the scope of the disclosure to employ implants having one or more openings to convey digestive fluids in the event that more than one duct delivers digestive fluids to the small intestines.

This application is also related to commonly assigned U.S. patent application Ser. Nos. 10/687,954; 10/778,365; and 10/799,512, the entirety of each of which is incorporated by reference.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

DETAILED DESCRIPTION

Embodiments of the present invention are described herein in the context of a minimally invasive gastrointestinal bypass.

Those of ordinary skill in the art will realize that the following detailed description of the present invention is illustrative only and is not intended to be in any way limiting. Other embodiments of the present invention will readily suggest themselves to such skilled persons having the benefit of this disclosure. Reference will now be made in detail to implementations of the present invention as illustrated in the accompanying drawings. The same reference indicators will be used throughout the drawings and the following detailed description to refer to the same or like parts.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

The present invention is a system, method, device, and apparatus to treat obesity through gastrointestinal bypass. By bypassing bodily fluids such as enzymatic, food, and other fluids to a location distal the GI tract, less food will be absorbed by the body and more food will be excreted, which results in weight loss.

Figure 1A:
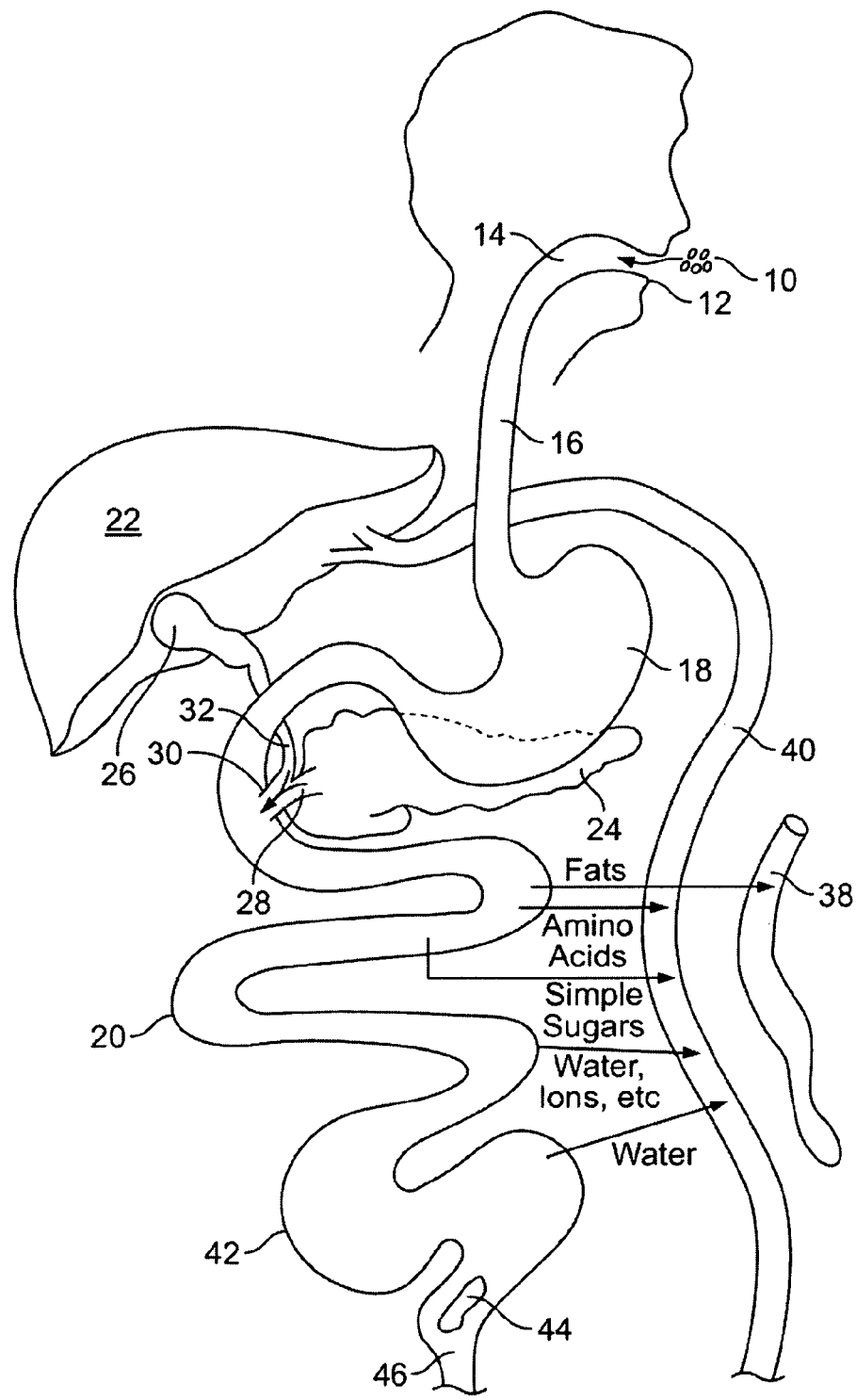
FIG. 1A is an illustration of the digestive system.
Figure 1B:
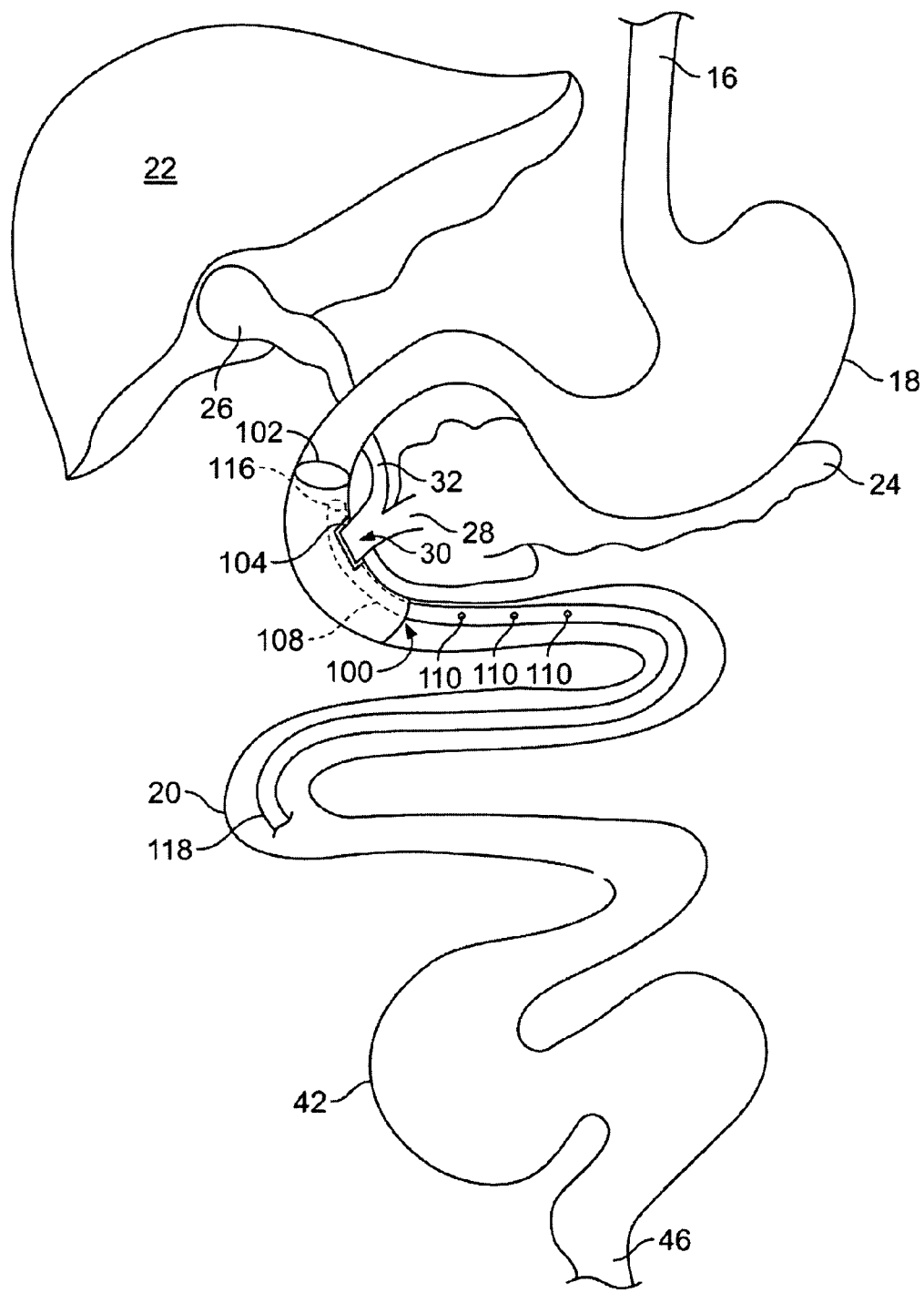
FIG. 1B is an illustration depicting a variation of the present invention when placed in the small intestines.

FIG. 1B illustrates a variation of an implant 100 for use in the present invention. As illustrated the implant diverts fluid from the duct 30 in the wall of the intestines. The implant 100 includes a support frame 102 that secures the implant within the intestines and a conduit 108 that diverts fluid from the duct 30. The support frame 102 can be selected from various structures such as tubes, stents, basket-type members, or other such structures or combination of structures that prevent migration of the implant 100 within the body.

The support frame 102 will include an opening 104 in a wall or side of the frame 102. The opening 104 will preferably be placed over the duct 30 to allow fluids to enter the conduit 108 and pass there through. It should be noted that the support frame 102 may be coated or have a tube placed there through to prevent fluids from passing through the wall of the support frame at any location other than the opening 104. Alternatively, the support frame 102 or portions thereof may be constructed to have a mesh or porous structure. Such a structure may aid in securing the implant within the intestinal wall. Furthermore, the implants of the present invention may have an antibacterial coating either on the support frame, on the barrier 120, on the elongate member 108, or in a combination of locations. The antibacterial coating may be used to prevent colonization of bacteria within the implant.

The support frame 102 may include anchors, ribs, protrusions, or other components (not illustrated) to aid in securing of the device. (For example, see U.S. Published Patent Applications 2004/0107004A1 and 2004/249362A1, the entirety of each of which is incorporated by reference. Such components may be solely located on the support frame 102. Alternatively, these components may also be located on the elongate member 108, either alone or in combination with fasteners on the support frame. Additional variations of the invention include an implant 100 which relies upon an adhesive to secure a portion or all of the implant 100 to the tissue wall. The adhesive or sealant may be any type that is used in medical procedures and may be used alone or in combination with the fastening components.

FIG. 1B also illustrates the elongate conduit as having a near portion 116 and a far portion 118. As discussed in more detail below, the near portion 116 may serve as a reservoir for fluids that would otherwise be blocked by food substances within the tract of the intestines. Accordingly, the near and far portions 116, 118 shall span across the opening 104 so that when food or other substances block the conduit in the far end (or distal to the opening), fluids exiting from the duct 30 may pass into the near end 116 of the elongate member 108 and subsequently pass from the implant 100 after clearing of the obstruction. Therefore, the near end portion 116 may serve as a reservoir for the implant 100. In many variations of the device 100, the near end 116 will be constructed to remain proximal to the opening 104.

The elongate conduit 108 illustrated in FIG. 1B can also include a number of openings or apertures 110 in the conduit body. Although the apertures 110 are optional, they may assist in preventing fluid from accumulating in the conduit 108 due to obstruction or constriction of the conduit 108. In some variations of the invention the implant 100 may comprise an absorbable substance placed over the apertures 110 so that fluid only exits the apertures 110 if there is a back flow due to fluid build-tip in the conduit 108. Alternatively, the apertures 110 may include valves that prevent food substances from entering the conduit 108 but allow fluid to exit due to a building of pressure in the conduit 108.

In some variations of the invention the implant 100 may include a conduit 108 comprised of a porous material or at least having a porous section to prevent accumulation of fluid or pressure. The conduit 108 may be comprised from a non-absorbable material or a bio absorbable material to provide a temporary placement within the intestines. Additional variations of the implant 100 may have multiple conduits 108 of the same or different lengths.

The conduit 108 of the present invention may have one or more lumens such that blockage of one lumen will not block the entire conduit 108. Accordingly, multiple tubes may be used or one or more multi-lumen tubes may be used.

In some variations of the invention, it may be desirable to size the lumen of the conduit 108 to be large enough in diameter such that the enzymes may pass through the conduit 108 without forming stones or causing infection. During placement of the implant 100, the conduit 108 may be compressed, folded, or rolled when implanted. To deploy the conduit 108 fluids, such as saline or gas may be inserted into the implant 100, through either the body portion 102 or the conduit 108 to extend, straighten, or unfurl the conduit into the GI tract. Such a feature may also be used to clear a blocked conduit 108 of any obstructions. However, it is also contemplated that the conduit 108 may unfurl itself by having the bile and pancreatic secretions fill the conduit or through intestinal peristalsis. Accordingly, the implant 100 may include a port or valve for allowing delivery of fluids to extend or clear the conduit 108.

The length of the conduit 108 may be selected such that it limits the interaction of digestive fluids as desired. The conduit 108 length at the distal end, away from the body, may be adjustable. The amount of malabsorption as a result of the conduit 108 is related to the length of the bowel pass by the conduit. Thus, the location of where the enzymatic fluids are to exit in the GI tract may be variable and may be determined by the doctor. The conduit 108 may be shortened by trimming its length prior to insertion into a patient's body.

In addition, the elongate member 108 may be sufficiently flexible to allow peristalsis to "milk" the elongate member to assist with moving the fluids there through. In additional variations of the invention, the elongate member 108 may be fabricated such that the interior walls of the member temporarily adhere together. This feature allows the elongate member 108 to serve as a fluid barrier and prevent reverse flow of substances within the implant.

Figure 2A:
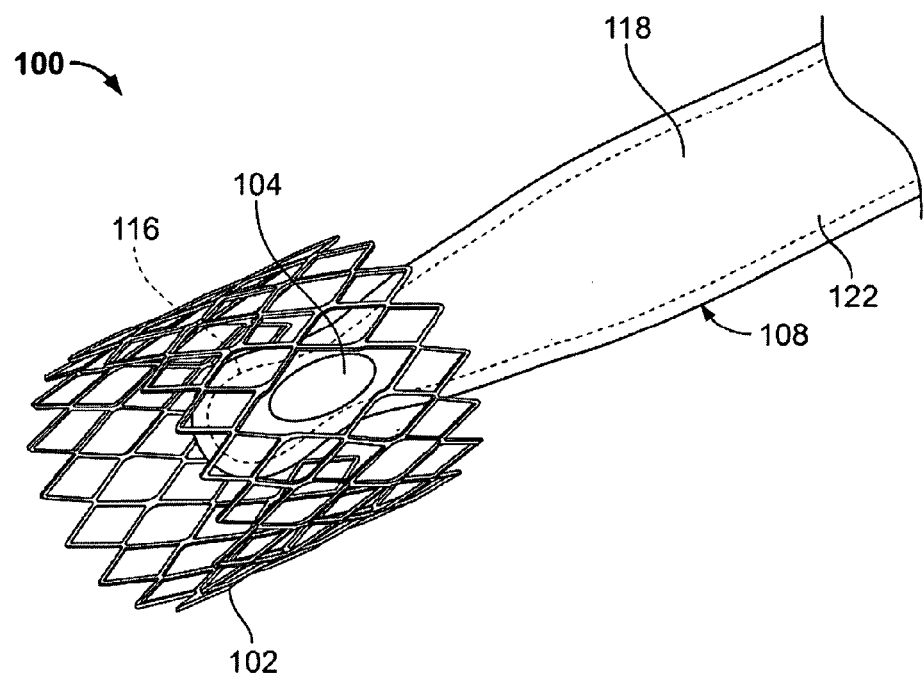
FIGS. 2A-2G represent variations of the invention.

FIGS. 2A-2D illustrate variations of implants 100. As shown in FIG. 2A, the implant includes a support frame 102 having an opening 104 in a side or wall. The opening is sized to allow for fluids to enter from, for example, the Ampula of Vater and pass into the conduit 108. As noted herein, the support frame may be a stent-type structure, a tube, or any similar structure that secures the implant within the small intestines and at the desired site. The support frame 102 may be constructed from a metal, alloy, shape-memory alloy, polymer, etc. The support frame 102 may be plastically deformable (such that a balloon or other mechanical expansion) deforms the frame 102 into place. Alternatively, it may be elastic such that it is restrained to conform to a small delivery profile and upon deployment is unrestrained to expand into place. In yet another variation, the support frame 102 may be a shape memory alloy and expand into shape upon reaching a particular temperature. In either case, it is important to note that variations of the invention include support frames 102 that are sufficiently elastic when implanted so that the support frame 102 expands within the bowel to permit passage of a food bolus without becoming dislodged. In this manner, the degree of expansion of the support frame 102 would be similar to that of the normal bowel.

Figure 2B:
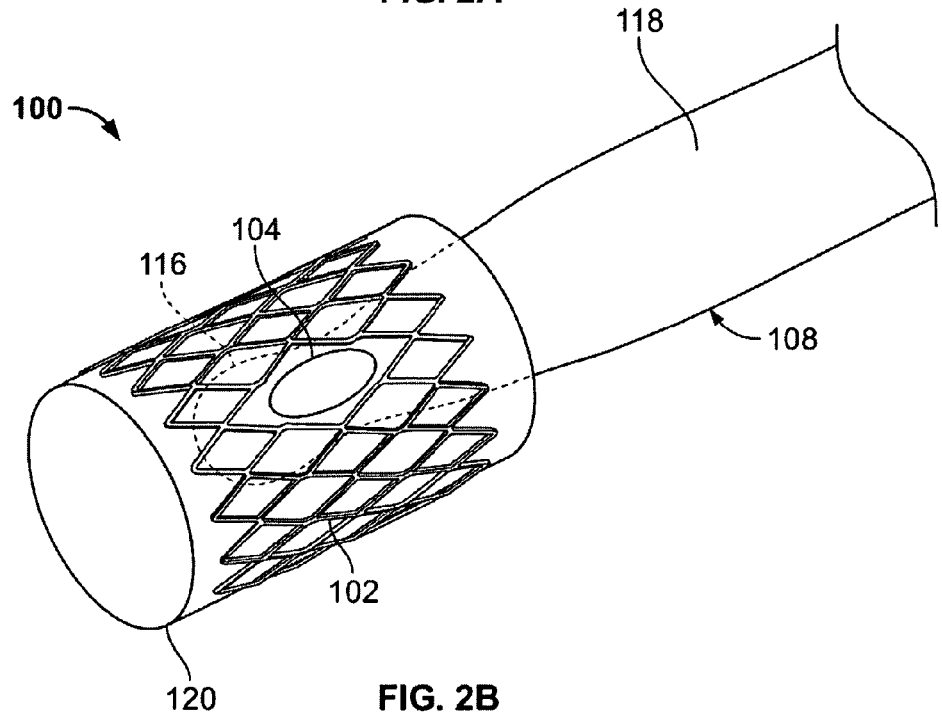

FIG. 2B illustrates another variation of an implant 100 where the support frame 102 includes a barrier 120. The barrier 120 may assist in directing fluids to the opening 104 or may provide a smooth internal surface for the support frame 102 to prevent food particles from becoming lodged within the frame 102. The barrier 120 may be formed from a polymer coating or may be the same material as the elongate member 108. For example, the barrier may comprise conduit comprises a polymer selected such as a thermoplastic polymer, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof.

The implant 100 further includes an elongate member 108 that is attached or otherwise coupled to the support frame 102 to allow fluids that enter the opening 104 to pass directly into a lumen of the conduit 108. The elongate member further includes a near portion 116 and a far portion 118 that span across the opening 104 to allow the near portion 116 to function as a reservoir.

Figure 2C:
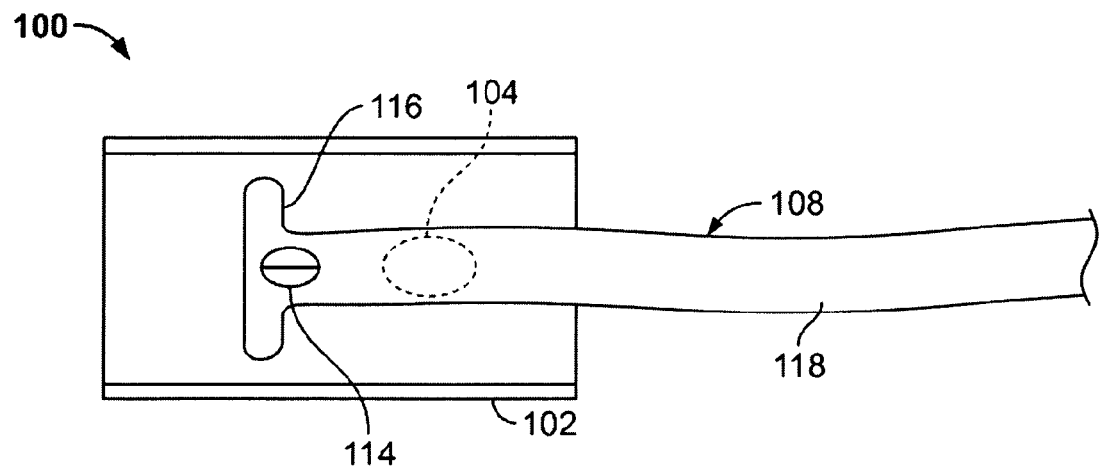

FIG. 2C illustrates a cross-sectional view of an implant 100. In this variation, the elongate member may include a valve 114 that allows for insertion of fluids to assist in deploying the far side 118 of the elongate member 108 or to remove blockages from the member 108. Such irrigation and/or inflation tubes used to assist in deploying or clearing the member may extend outside of the mouth or body in those cases where frequent irrigation is required. In this variation, the near portion 116 of the elongate member 108 comprises a "T" shape. It should be understood that the invention may comprise any shape that allows for the near portion 116 to function as a reservoir.

Figure 2D:
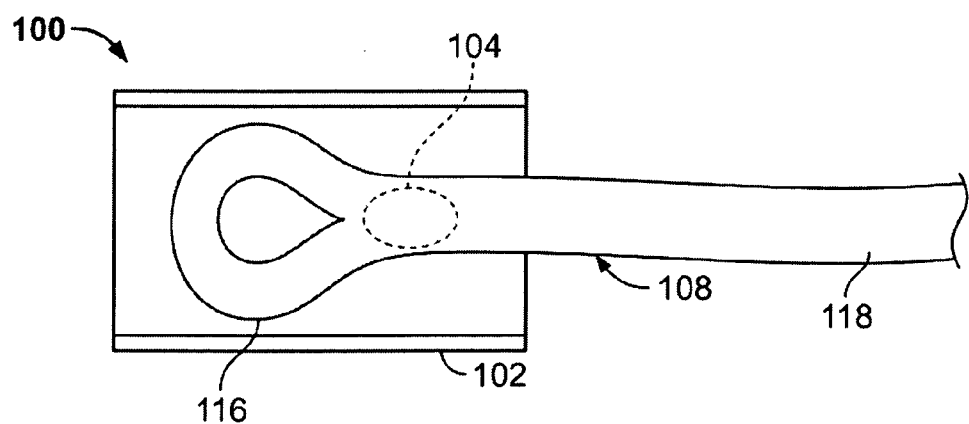

FIG. 2D illustrates a cross-sectional view of another variation of an implant 100. In this variation of the invention, the near portion 116 comprises a loop shape. Though not shown, the near portion 116 can be secured to the support frame 102 such that it remains in the near or proximal section of the frame 102.

The near portions 116 described herein may be fabricated with a profile that minimizes interference with substances passed from the stomach through the intestines. In one variation of the invention, the near portions 116 may have a low profile so as not to create a point of obstruction at the proximal end of the implant that accumulates food and other particles within the small intestines. Moreover, the near portion 116 may be fabricated to have a thinner wall thickness than the remainder of the conduit 108.

Figure 2E:
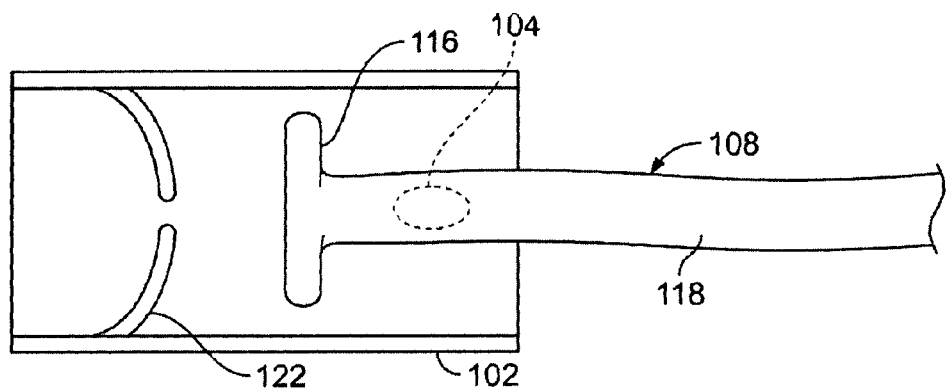
Figure 2F:
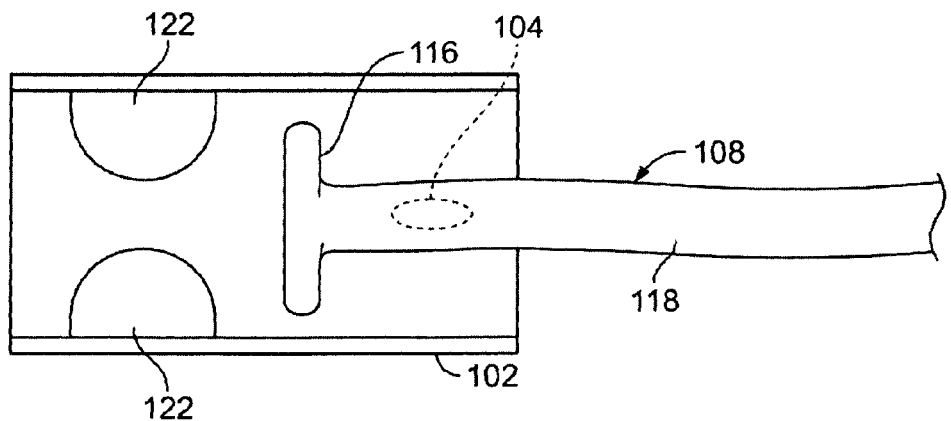

The implant 100 may further include a restricting portion 122. The restricting portion 122 may be used to reduce the rate of gastric emptying. The restricting portion 122 illustrated in FIG. 2E may be one or more baffles, valves, funnels, etc. that reduce the size in a portion of the implant 100. The restricting portion 122 may be a part of the support frame or inserted into the support frame after deployment into the bowels. Alternatively, as shown in FIG. 2F, the restricting portion 122 may comprise one or more inflatable members such as a bladder or balloon. Accordingly, the restricting portion 122 may be inflated to a desired size after implantation of the support frame 102. The restriction member 122 may be a valve.

Figure 2G:
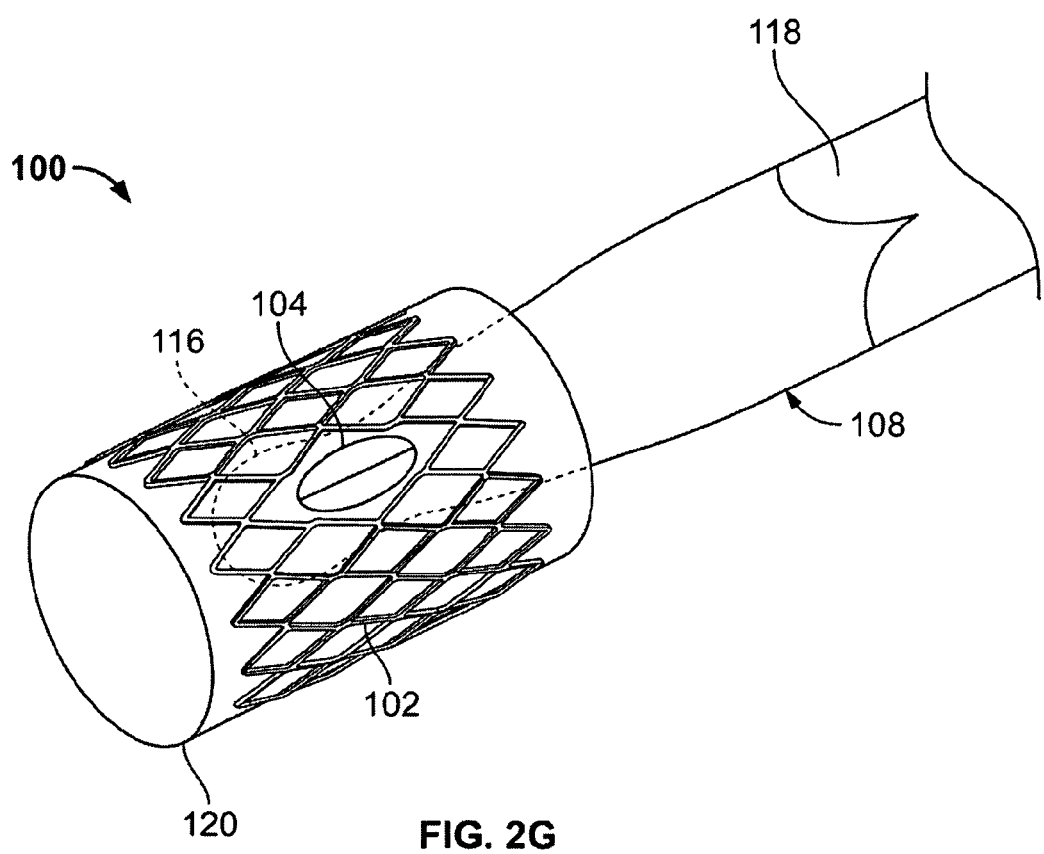

FIG. 2G shows another variation of the invention. In this variation the aperture 104 and/or the conduit 108 may include a valve. The valve may also be located in one or more apertures 110.

Figure 3A:
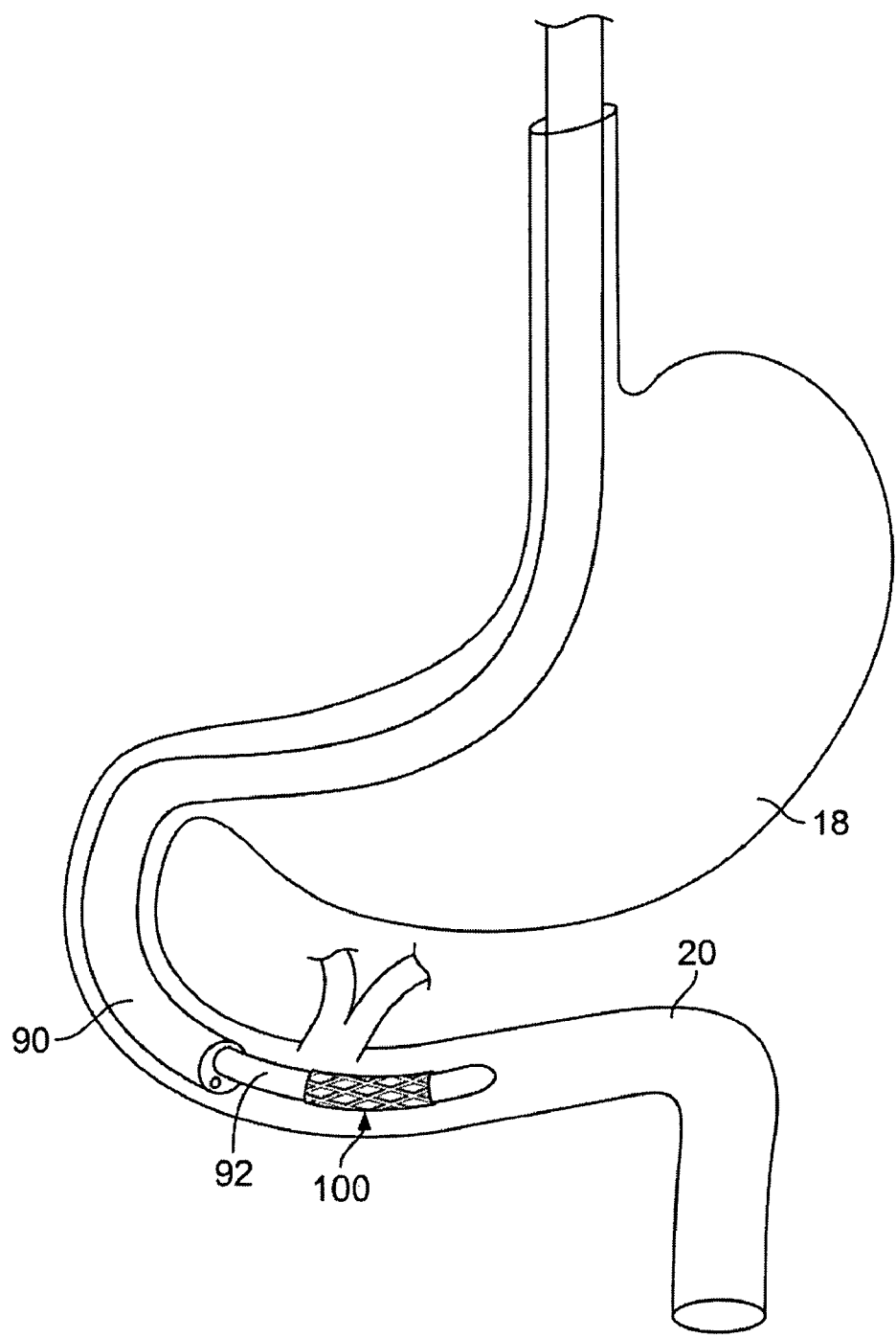
FIGS. 3A-3D represent schematics of a variation of the present invention when placed and during passage of food-substances within the small intestines.

FIG. 3A illustrates advancement of an implant 100 according to the present invention to a site within the small intestines 20. As shown, the implant 100 may be mounted on a delivery catheter 92. Use of a scope 90 is optional but preferred. The implant 100, catheter 92, and/or scope 90 may have a mark or other indicator to aid the operator in aligning the opening (not shown) with the Ampula of Vater 30. Preferably, during deployment, the far end of the elongate member (not shown) is folded or otherwise placed within the implant 100 or delivery catheter 92.

Figure 3B:
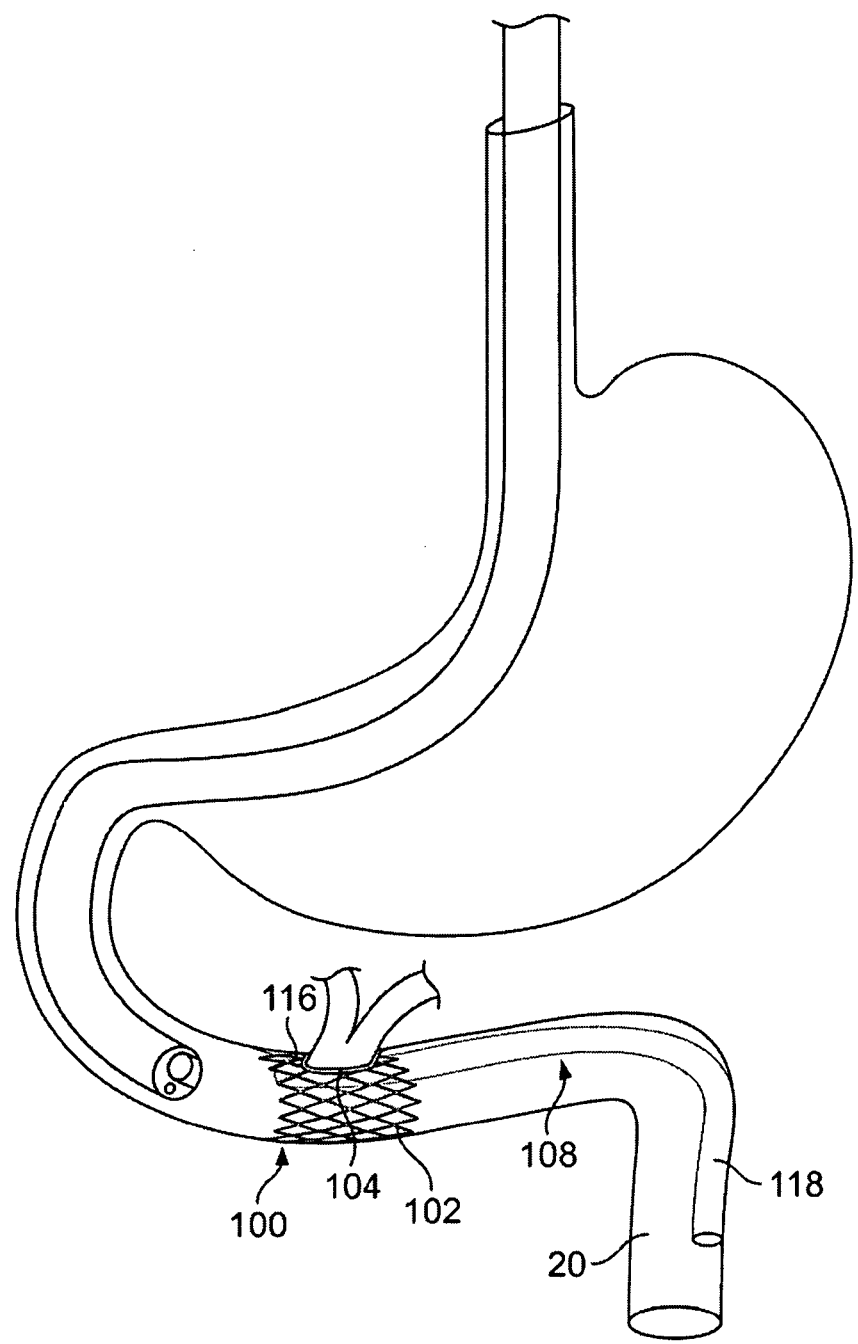

FIG. 3B illustrates the implant 100 after placement within the small intestines 20. Although not shown, the implant 100 may be placed with the use of a balloon or other expansion means. Alternatively, the implant may self-expand to fit within the small intestines 20. Fluid may be used to deploy the far end 118 of the elongate member 108 distally in the small intestines 20. However, the elongate member 108 may self-deploy over time. As shown, the near portion 116 of the implant 100 is located proximal to the opening 104. The far portion 118 of the elongate member 108 is placed distally in the intestines so that the near and far portions 116 and 118 span across the opening 104.

Figure 3C:
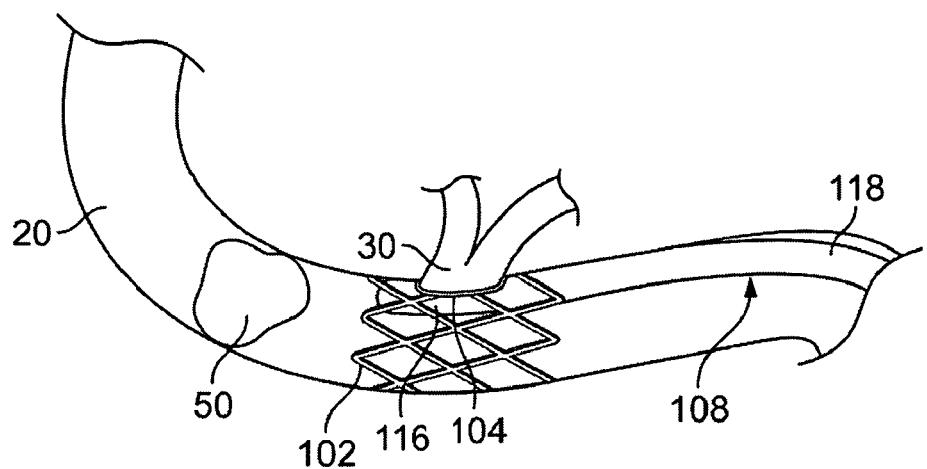
Figure 3D:
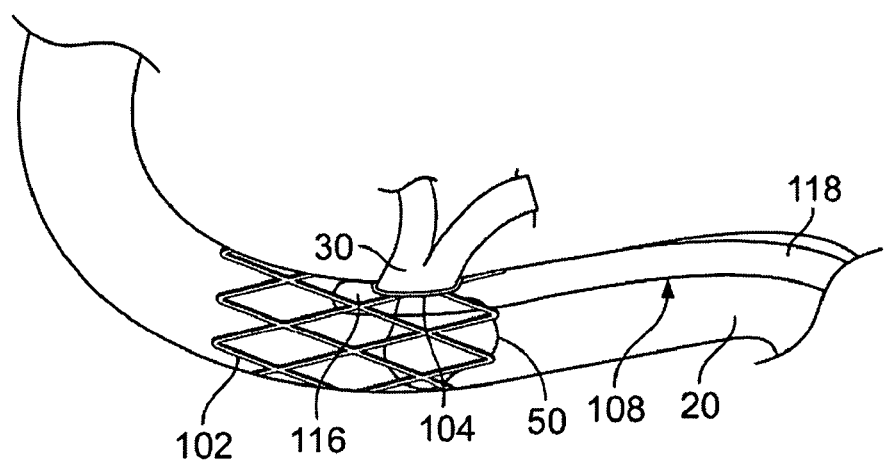

FIG. 3C is a schematic that illustrates a principle of the invention. As shown, a bolus 50 of food travels through the small intestines. As shown in FIG. 3D, as the bolus 50 passes adjacent to or distal to the Ampula of Vater 30, the bolus 50 blocks the conduit 108. However, the digestive fluids continue to enter the conduit 108 via the opening 104. Thus, the near section 116 of the elongate member 108 serves as a reservoir and captures the digestive fluids that would otherwise be blocked due to the bolus 50. It should be noted that as subsequent food particles pass through the small intestines, the digestive fluids located in the near portion 116 are forced towards the far end 118 of the conduit 108. Typically, the Ampula of Vater 30 has a valve that prevents the digestive fluid from passing back into the duct.

Various means may be employed to restrain the support frame 102 and/or elongate member 108 within the intestines.

Such means may include wire or polymeric strands, sleeve-like devices, or woven mesh strictures to tie the support frame 102.

The polymers for use in the present invention may include polymers such as thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof. Moreover, variations of the invention include an implant where the body portion comprises a bioabsorbable polymer.

As described herein, the device 100 shortens the effective absorption length of the bowel or GI tract. The effective absorption is the amount of digested food that is absorbed by the body. By bypassing the bodily fluids in the GI tract, such as bile and pancreatic enzymes, to a location further downstream within the GI tract, nutrients from the food fluid will not be absorbed by the enzymes or emulsifying reagents in the body as it travels from the stomach and through the intestine. This will also reduce the absorption time of the food fluids into the body. Thus, the effective absorption of nutrients from the food fluids is decreased whereby most of the food fluids are excreted which results in the patient's weight loss.

The conduit 108 may be a flexible tube having a first end configured to divert enzymatic fluids to a location significantly further down the GI tract. In variations of the invention, the end of the conduit is closed and acts as a reservoir for fluid entering from the side opening. The conduit 108 may be large enough in diameter such that the enzymes may pass through the flexible tube without forming stones or becoming infected. In an alternative embodiment, the conduit may contain a plurality of apertures 110 to allow some enzymatic fluids to pass through to prevent injury or death to the patient should the conduit become clogged. The conduit 108 may also have a side port (not shown) to allow fluids, such as saline, or gas to pass through the conduit to extend, straighten, or unfurl the conduit into the GI tract as will be further described below. This may also ensure that the lumen of the conduit is free and clear of any obstructions. However, the conduit may unfurl itself by having the bile and pancreatic secretions fill the conduit or through intestinal peristalsis.

The length of the conduit 108 at the far portion 118 may be adjustable depending on the needs of the patient. Since the amount of malabsorption as a result of the implant 100 relates to the length of the bowel by-pass (i.e., the length of the conduit 108), having the ability to adjustment the length of the conduit 108 may be desirable. In other words, the location to where the enzymatic fluids are bypassed in the GI tract may be variable and may be determined by the doctor. Additionally, the conduit 100 may be comprised of a structure that adjusts in length after implantation (e.g., a filamentous member may be attached to the conduit such that when the filamentous member is pulled, the conduit 108 shortens accordion style.)

By modifying the location at which enzymatic fluids interact with nutrients from food fluids in the GI tract the body absorbs less nutrients from food fluids. As a result, the effectiveness of enzyme and emulsifying reagent reacting with the food fluids decreases, and more of the food fluids are excreted. The end effect results in weight loss by the patient having the implant. The invention changes the proportion of absorbed food fluids to excreted food fluids causing the weight loss. Additionally, as is apparent, the patient may continue to consume the same amount of food, but use of the device allows for weight loss.

Figure 4:
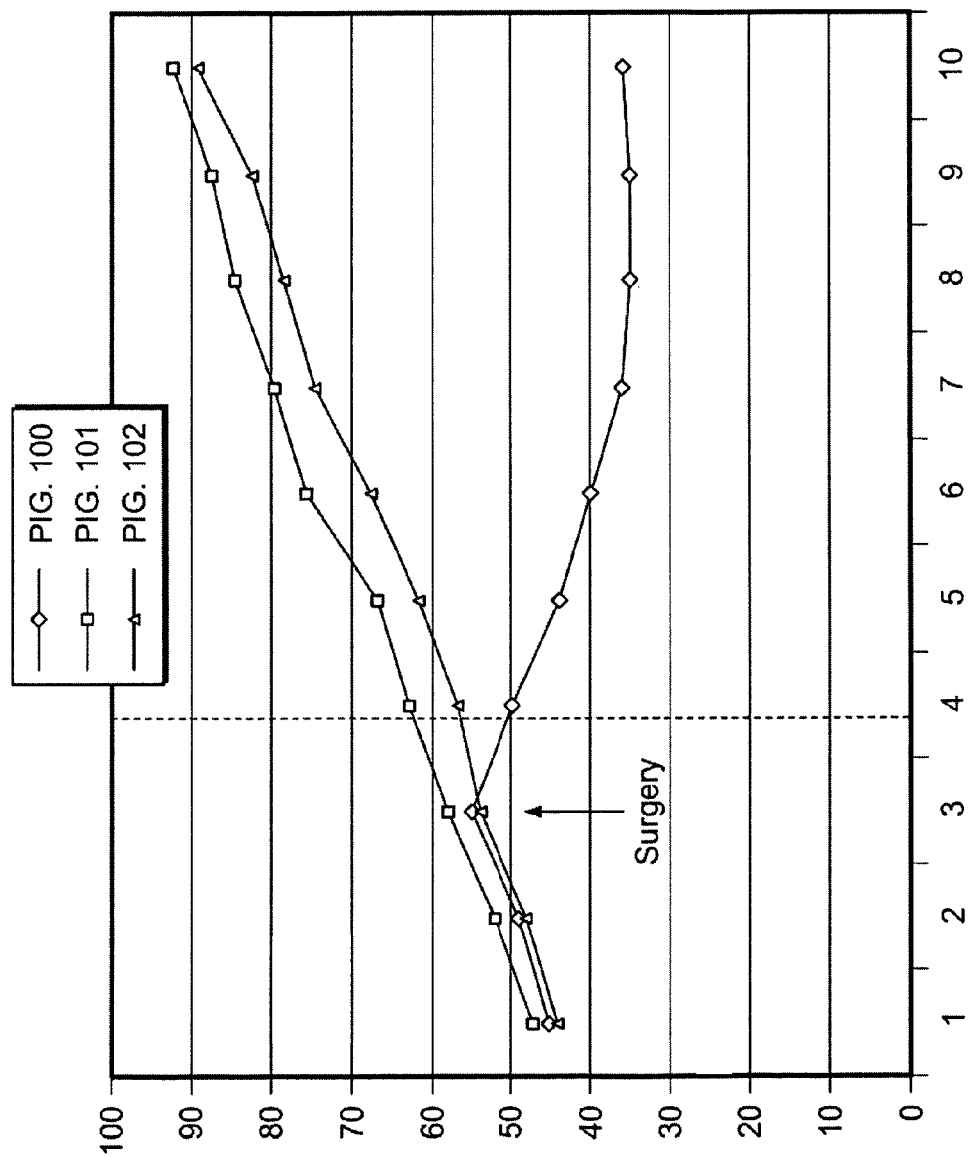
FIG. 4 is a graph illustrating data obtained from testing of a similar device in an animal model.

FIG. 4 is a graph illustrating data obtained from testing the device in a pig animal model. The Y-axis is weight in Kilograms and the X-axis is time in weeks. Pigs A, B, and C consumed the same amount of food throughout the testing period. Pigs B and C were controls (the device was not implanted in these animals). In the experiment, Pig A was implanted with a variation of the invention at week 3. At this time all pigs weighed between 54-59 kilograms. After implantation of the device, Pig A rapidly lost weight in weeks 3 through 7 going from 55 kilograms to 36 kilograms while pigs B and C continued to gain weight. Data after week 7 indicates that Pig A maintained a constant weight at about 35 kilograms for several weeks thereafter. Although Pig A continued to consume the same amount of food each day similar to Pigs B and C, Pig A maintained the lost weight.

It is contemplated that the implant 100 may be inserted into a patient without major surgery, incisions, or the use of general anesthesia. Rather, the patient may be sedated when the device is to be delivered through the mouth of a patient. The length of the device may be adjusted, if necessary, based upon the judgment of the physician or other factors such as the desired weight loss, etc. The length of the conduit may be trimmed or cut by any means. The device is then fitted onto an endoscope. The device may be inserted either prior to inserting the endoscope into the patient's mouth or after insertion of the endoscope into the patient's mouth. However, the device may be formed in any shape possible that would allow for the easiest and safest means to place the device into the patient. By way of example only, and not intended to be limiting, the device may be rolled-up onto itself, the device may be folded into a fan shape, or the device may be folded into a zigzag shape before insertion into the patient's body.

An endoscope locates the placement site (e.g., the Ampula of Vater) for the implant. A retractor may be inserted into the Ampula of Vater. The retractor may have an expandable balloon or a fenestrated tube that may be activated with a vacuum suction to suction the tissue around the Ampula into contact with the body portion. However, other methods of retraction are possible such as a corkscrew that may be screwed into the tissue or a multiple-tined piercing device.

As discussed above, the conduit may have a side port to allow fluids, such as saline, or gas to pass through the conduit to extend, straighten, or unfurl the conduit into the GI tract. This ensures that the lumen of the conduit is free and clear of any obstructions. However, the conduit may unfurl itself by having the bile and pancreatic secretions fill the conduit or through intestinal peristalsis.

The device may be easily removed from the patient's body. Alternatively, the device may remain in the patient's body, but the length of the conduit may be adjusted.

In addition to assisting in controlling obesity, the implants of the present invention may also be used to aid in diabetes management. For example, placement of the implants in patients with diabetes may serve to reduce glucose intolerance and/or insulin resistance by bypassing fluids within the bowels in the manner described above.

While embodiments and applications of this invention have been shown and described, it would be apparent to those skilled in the art having the benefit of this disclosure that many more modifications than mentioned above are possible without departing from the inventive concepts herein. The invention, therefore, is not to be restricted except in the spirit of the appended claims. Furthermore, the above illustrations are examples of the invention described herein. Because of the scope of the invention, it is specifically contemplated that combinations of aspects of specific embodiments or combinations of the specific embodiments themselves are within the scope of this disclosure.

I claim:

1. A method for diverting fluid from a duct in a wall of a small intestines, the method comprising:
   inserting a support frame into the small intestines, the support frame having an opening in a wall and having an elongate conduit member coupled the support frame where the support frame further includes a barrier preventing fluid from passing through the wall of the support frame at any location other than the opening;
   the elongate conduit having a near portion and a far portion and a lumen extending therebetween, where the lumen is in fluid communication with the side opening of the support frame at a location between the near and far portions causing the near portion and far portion of the conduit span across the side opening in the support frame such that the near portion remains proximal to the side opening, the elongate conduit further having at least one distal opening in the far portion; and
   aligning the side opening with the duct such that fluid from the duct enters the elongate conduit lumen.

2. The method of claim 1, where the barrier comprises a coating on the support frame.

3. The method of claim 1, where the barrier comprises a tube coaxially located with the support frame.

4. The method of claim 1, where blockage of the lumen by food substance at a location adjacent or distal to the duct causes flow of fluid from the duct into the near portion of the elongate member.

5. The method of claim 1, where the support frame comprises a stent.

6. The method of claim 1, where the support frame comprises a sleeve.

7. The method of claim 1, where the support frame is self-expanding.

8. The method of claim 1, where the support frame is plastically deformable and where aligning the side opening with the duct comprises expanding the support frame to contact the small intestines.

9. The method of claim 1, where the support frame is elastically deformable and is in a compressed state prior to inserting into the small intestines and is in an expanded state after aligning the side opening with the duct.

10. The method of claim 1, where aligning the side opening with the duct comprises aligning the side opening with an Ampula of Vater.

11. The method of claim 1, further comprising locating the far end of the elongate conduit within the small intestines and at a distance from the support frame.

12. The method of claim 1, where the conduit further includes a plurality of apertures within a body of the conduit.

13. The method of claim 1, where at least one of the plurality of apertures is covered by a bioabsorbable polymer.

14. The method of claim 1, where the conduit is flexible and comprises a polymer selected from a group consisting of thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof.

15. The method of claim 1, where the support frame is located on a balloon catheter, and further comprising inflating the balloon to expand the support frame.

16. The method of claim 1, where the support frame is located on a catheter and restrained in a delivery state, catheter, and where expanding the support frame comprises unrestraining the support frame.

17. The method of claim 1, where the support frame comprises a shape memory alloy, and where upon reaching body temperatures, the support frame expands against the small intestine wall such that fluid exiting the duct passes directly into the elongate conduit lumen.

18. The method of claim 1, where the flexible conduit comprises a porous material such that upon an increase in pressure within the conduit intestinal fluids exit the conduit through the porous material.

19. The method of claim 1, where the support frame comprises a bioabsorbable material.

20. The method of claim 1, where the conduit comprises a bioabsorbable material.

21. The method of claim 1, where the conduit lumen or side opening includes a valve.

22. The method of claim 1, further comprising removing the support member and elongate member.

23. An implant for diverting fluid from a duct within a small intestines, the implant comprising:
 a support frame having a wall defining a passageway, where the wall includes at least one opening in the wall where the wall opening is sized greater than that of an adult Ampula of Vater;
 an elongate conduit having a near portion and a far portion and body extending therebetween, a lumen extending therebetween, where the lumen is in fluid communication with the side opening of the support frame at a location between the near and far portions causing the near portion and far portion of the conduit to span across the side opening in the support frame such that the near portion remains proximal to the side opening, and at least one distal opening in the far portion of the elongate member.

24. The implant of claim 23, where the support frame further includes a barrier preventing fluid from passing through the wall of the support frame at any location other than the opening.

25. The implant of claim 24, where the barrier comprises a coating on the support frame.

26. The implant of claim 24, where the barrier comprises a tube coaxially located with the support frame.

27. The implant of claim 23, where the support frame comprises a shape memory alloy.

28. The implant of claim 23, where the shape memory alloy comprises a super-elastic material.

29. The implant of claim 23, where the elongate conduit comprises a polymer selected from a group consisting of thermoplastic polymers, thermoset polymers, acrylate polymers, a blend of acrylate-methacrylate polymers, silicone elastomers, urethane elastomers, ethylene vinyl acetate polymers, polyethylene, polypropylene, PLA-PGA, PLA, PGA, polyortho-ester, polycapralactone, polyester, hydrogels, polystyrene, co-polymers of styrene-isobutylene-styrene, and combinations or blends thereof.

30. The implant of claim 23, where the elongate conduit body comprises a length sufficient to limit the interaction of intestinal fluids with food product.

31. The implant of claim 23, where the elongate conduit body comprises a porous material such that upon an increase in pressure within the conduit intestinal fluids exit the conduit through the porous material.

32. The implant of claim 23, where a thickness of the near portion of the elongate body is less than a thickness of the far portion such that food product encounters low resistance as it flows past the body.

33. The implant of 23, where the elongate conduit claim 1, where the flexible conduit body comprises a bioabsorbable material.

34. The implant of claim 23, where the flexible conduit body comprises a bioabsorbable material.

35. The implant of claim 23, further comprising at least one aperture opening in the flexible conduit body.

36. The implant of claim 35, where at least one aperture is covered by a bioabsorbable polymer.

37. The implant of claim 35, where at least one aperture includes a valve.

38. The implant of claim 23, where the distal opening is located at an end of the far portion.

39. The implant of claim 23, where the near portion comprises a T shape or a loop.

* * * * *